(12) United States Patent
Murphy et al.

(10) Patent No.: US 7,718,825 B2
(45) Date of Patent: *May 18, 2010

(54) ARYLAMINE PROCESS

(75) Inventors: Leanne D. Murphy, Etobicoke (CA);
Sarah J. P. Robinson, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 810 days.

This patent is subject to a terminal disclaimer.

(21) Appl. No.: 11/277,740

(22) Filed: Mar. 28, 2006

(65) Prior Publication Data

US 2007/0232830 A1  Oct. 4, 2007

(51) Int. Cl.
*C07C 229/44* (2006.01)

(52) U.S. Cl. .................................... 562/457

(58) Field of Classification Search ........... None
See application file for complete search history.

(56) References Cited

U.S. PATENT DOCUMENTS

| | | | | |
|---|---|---|---|---|
| 3,567,450 | A | * | 3/1971 | Brantley et al. ............... 430/73 |
| 4,265,990 | A | | 5/1981 | Stolka et al. |
| 4,617,373 | A | * | 10/1986 | Pruett et al. ................. 528/288 |
| 6,730,448 | B2 | | 5/2004 | Yoshino et al. |
| 2004/0086794 | A1 | | 5/2004 | Yamada et al. |
| 2005/0234272 | A1 | | 10/2005 | Goodbrand et al. |
| 2006/0025631 | A1 | | 2/2006 | Bender et al. |

FOREIGN PATENT DOCUMENTS

| | | |
|---|---|---|
| JP | A 57-128344 | 8/1982 |
| JP | B2 60-22347 | 6/1985 |
| JP | A-63-65449 | 3/1988 |
| JP | A-4-15659 | 1/1992 |
| JP | B2 5-47104 | 7/1993 |

OTHER PUBLICATIONS

Wiles et al: Tetrahedron Letters (2006), 47(30), 5261-5264.*
Archer, Organic Syntheses, Coll. vol. 4, 1963, p. 331.*
Li et al. Synthetic communications, 2001, 31(5), 653-656.*
Yang et al. Catalysis Communications 2004, 5, 75-78.*
A.R. Khosropour, et al., "Synthesis of trans-cinnamic acids from aryl aldehydes and aryl aldehyde bisulfate adducts with malonic acid using piperazine," J. Chem. Res., 6, 364-365 (2005).
F.S. Prout, et al., "Catalyst Study of the Knoevenagel Condensation," J. Chem. Eng. Data, 8(4), 597-599 (1963).
U.S. Appl. No. 10/992,658, filed Nov. 22, 2004, Goodbrand et al.
U.S. Appl. No. 10/992,687, filed Nov. 22, 2004, Bender et al.

(Continued)

*Primary Examiner*—Daniel M Sullivan
*Assistant Examiner*—Yevegeny Valenrod
(74) *Attorney, Agent, or Firm*—Oliff & Berridge, PLC

(57) ABSTRACT

A process for converting an arylamine into an arylamine derivative, includes (i) providing a first arylamine compound; (ii) formylating the first arylamine compound to form a formyl substituted arylamine compound, where the first arylamine compound is not a formyl substituted arylamine compound; and (iii) acidifying the formyl substituted arylamine compound, in the presence of a solvent and a solid organic catalyst, to convert formyl functional groups into acid functional groups to form an acidified compound.

27 Claims, 2 Drawing Sheets

OTHER PUBLICATIONS

U.S. Appl. No. 10/992,690, filed Nov. 22, 2004, Bender et al.
U.S. Appl. No. 10/998,585, filed Nov. 30, 2004, Bender et al.
U.S. Appl. No. 11/034,713, filed Jan. 14, 2005, Yu Qi et al.
U.S. Appl. No. 11/094,683, filed Mar. 31, 2005, H. Bruce Goodbrand et al.
U.S. Appl. No. 11/263,671, filed Nov, 1, 2005, Timothy P. Bender et al.

* cited by examiner

ARYLAMINE PROCESS

TECHNICAL FIELD

This disclosure is generally directed to processes for the synthesis of arylamine compounds, and to the use of such compounds in electrophotographic imaging members. In particular, this disclosure provides a process for forming a 4-aminobiphenyl derivative arylamine compound, such as N,N-[3-carboxypropyl phenyl]-4-aminobiphenyl, or a triarylamine derivative, or their alkali metal salts, using an improved Knoevenagel reaction.

RELATED APPLICATIONS

Commonly assigned, U.S. patent application Ser. No. 11/263,671 filed Nov. 1, 2005, describes a process for the preparation of a tertiary arylamine compound, comprising reacting an arylhalide and an arylamine in an ionic liquid in the presence of a catalyst.

Commonly assigned, U.S. patent application Ser. No. 10/9392,690 filed Nov. 22, 2004, describes a process for forming a tertiary arylamine compound, comprising reacting an arylbromide and an arylamine. For example, the application describes a process for forming N,N-diphenyl-4-aminobiphenyl, comprising reacting 4-bromobiphenyl and diphenylamine in the presence of a palladium-ligated catalyst.

Commonly assigned, U.S. patent application Ser. No. 10/992,687 filed Nov. 22, 2004, describes a process for forming a 4-aminobiphenyl derivative arylamine compound, comprising: (i) providing a first disubstituted 4-aminobiphenyl compound; (ii) optionally formylating the first disubstituted 4-aminobiphenyl compound to form a bisformyl substituted compound, where the first disubstituted 4-aminobiphenyl compound is not a bisformyl substituted compound; (iii) acidifying the bisformyl substituted compound to convert formyl functional groups into acid functional groups to form an acidified compound; and (iv) hydrogenating the acidified compound to saturate at least one unsaturated double bonds in the acidified compound, wherein there is provided a second disubstituted 4-aminobiphenyl compound.

Commonly assigned, U.S. patent application Ser. No. 10/992,658 filed Nov. 22, 2004, describes a process for forming a 4-aminobiphenyl derivative arylamine compound, comprising: (i) providing an iodinated organic compound; (ii) substituting the iodinated organic compound at carboxylic acid groups thereof to provide ester protecting groups; (iii) conducting an Ullman condensation reaction to convert the product of step (ii) into an arylamine compound; and (iv) conducting a Suzuki coupling reaction to add an additional phenyl group to the arylamine compound in the 4-position relative to the nitrogen, to provide the 4-aminobiphenyl derivative arylamine compound.

Commonly assigned, U.S. patent application Ser. No. 11/094,683 filed Mar. 31, 2005, describes a process for forming an anhydrous alkali earth salt of a dicarboxylic acid of an arylamine compound, comprising reacting a dicarboxylic acid of an arylamine compound with an anhydrous alkali earth salt. The application also discloses a process for forming a siloxane-containing hole-transport molecule, comprising: reacting a dicarboxylic acid of an arylamine compound with an anhydrous alkali earth salt to form an anhydrous dicarboxylic acid salt of the arylamine compound; and reacting the anhydrous dicarboxylic acid salt of the arylamine compound with a siloxane-containing compound.

Commonly assigned, U.S. patent application Ser. No. 10/998,585 filed Nov. 30, 2004, describes a silicon-containing layer for electrophotographic photoreceptors comprising: one or more siloxane-containing compound; and one or more siloxane-containing antioxidiant; wherein the siloxane-containing antioxidant is at least one member selected from the group consisting of hindered-phenol antioxidants, hindered-amine antioxidants, thioether antioxidants and phosphite antioxidants.

Commonly assigned, U.S. patent application Ser. No. 11/034,713 filed Jan. 14, 2005, describes an electrophotographic photoreceptor comprising a charge-generating layer, a charge-transport layer, and an overcoat layer comprised of a crosslinked siloxane composite composition comprising at least one siloxane-containing compound and metal oxide particles.

Commonly assigned, U.S. patent application Ser. No. 10/709,193 filed Apr. 20, 2004, describes a process for preparing an aryl iodide compound, comprising: reacting an aryl halide compound with a metal iodide, a metal catalyst and a catalyst coordinating ligand in at least one solvent to form an aryl iodide; and purifying the aryl iodide; wherein the solvent is heated to reflux during the reacting; wherein an aryl iodide yield of at least about 75% is obtained; and wherein the aryl iodide has a purity of at least 90%.

The appropriate components and process aspects of each of the foregoing, such as the arylamine precursor materials and electrophotographic imaging members, may be selected for the present disclosure in embodiments thereof. The entire disclosures of the above-mentioned applications are totally incorporated herein by reference.

REFERENCES

JP-A-63-65449 (the term "JP-A" as used herein means an "unexamined published Japanese patent application"), discloses an electrophotogtaphic photoreceptor in which fine silicone particles are added to a photosensitive layer, and also discloses that such addition of the fine silicone particles imparts lubricity to a surface of the photoreceptor.

Further, in forming a photosensitive layer, a method has been proposed in which a charge transport substance is dispersed in a binder polymer or a polymer precursor thereof, and then the binder polymer or the polymer precursor thereof is cured. JP-B-5-47104 (the term "JP-B" as used herein means an "examined Japanese patent publication") and JP-B-60-22347, disclose electrophotographic photoreceptors using silicone materials as the binder polymers or the polymer precursors thereof.

Furthermore, in order to improve mechanical strength of the electrophotographic photoreceptor, a protective layer is formed on the surface of the photosensitive layer in some cases. A cross-linkable resin is used as a material for the protective layer in many cases. However, the protective layer formed by the cross-linkable resin acts as an insulating layer, which impairs the photoelectric characteristics of the photoreceptor. For this reason, a method of dispersing a fine conductive metal oxide powder (JP-A-57-128344) or a charge-transport substance (JP-A-4-15659) in the protective layer and a method of reacting a charge-transport substance having a reactive functional group with a thermoplastic resin to form the protective layer have been proposed.

However, even the above-mentioned conventional electrophotographic photoreceptors are not necessarily sufficient in electrophotographic characteristics and durability, particularly when used in combination with a charger of the contact-charging system (contact charger) or a cleaning apparatus, such as a cleaning blade.

Further, when a photoreceptor is used in combination with a contact charger and a toner obtained by chemical polymerization (polymerization toner), a surface of the photoreceptor may become stained with a discharge product produced in contact charging or with polymerization toner that remains after a transport step. This staining can deteriorate image quality in some cases. Still further, use of a cleaning blade to remove discharge product or remaining toner adhered to the photoreceptor surface increases friction and abrasion between the surface of the photoreceptor and the cleaning blade, resulting in a tendency to cause damage to the surface of the photoreceptor, breakage of the blade or turning up of the blade.

Furthermore, in producing a photoreceptor, in addition to improvement in electrophotographic characteristics and durability, reducing production costs becomes an important problem. However, conventional electrophotographic photoreceptors also may have problems relating to coating defects such as orange peel appearances and hard spots.

The use of silicon-containing compounds in photoreceptor layers, including in photosensitive and protective layers, has been shown to increase the mechanical lifetime of electrophotographic photoreceptors, under charging conditions and scorotron charging conditions. For example, U.S. Patent Application Publication US 2004/0086794 to Yamada et al. discloses a photoreceptor having improved mechanical strength and stain resistance.

However, the above-mentioned conventional electrophotographic photoreceptor is not necessarily sufficient in electrophotographic characteristics and durability, particularly when such a photoreceptor is used in an environment of high heat and humidity.

Photoreceptors having low wear rates, such as those described in Yamada, also have low refresh rates. The low wear and refresh rates are a primary cause of image-deletion errors, particularly under conditions of high humidity and high temperature. U.S. Pat. No. 6,730,448 B2 to Yoshino et al. addresses this issue, disclosing photoreceptors having some improvement in image quality, fixing ability, even in an environment of high heat and humidity. However, there still remains a need for electrophotographic photoreceptors having high mechanical strength and improved electrophotographic characteristics and improved image deletion characteristics even under conditions of high temperature and high humidity.

The disclosures of each of the foregoing patents and publications, and the disclosures of any patents and publications cited below, are hereby totally incorporated by reference. The appropriate components and process aspects of the each of the foregoing patents and publications may also be selected for the present compositions and processes in embodiments thereof.

BACKGROUND

In electrophotography, an electrophotographic substrate containing a photoconductive insulating layer on a conductive layer is imaged by first uniformly electrostatically charging a surface of the substrate. The substrate is then exposed to a pattern of activating electromagnetic radiation, such as, for example, light. The electromagnetic radiation selectively dissipates charge in illuminated areas of the photoconductive insulating layer while leaving behind an electrostatic latent image in non-illuminated areas of the photoconductive insulating layer. This electrostatic latent image is then developed to form a visible image by depositing finely divided electroscopic marking particles on the surface of the photoconductive insulating layer. The resulting visible image is then transferred from the electrophotographic substrate to a necessary member, such as, for example, an intermediate-transfer member or a print substrate, such as paper. This image developing process can be repeated as many times as necessary with reusable photoconductive insulating layers.

In image-forming apparatus such as copiers, printers and facsimiles, electrophotographic systems in which charging, exposure, development, transfer, etc. are carried out using electrophotographic photoreceptors have been widely employed. In such image-forming apparatus, there are ever-increasing demands for speeding up of image-formation processes, improvement in image quality, miniaturization and prolonged life of the apparatus, reduction in production cost and running cost, etc. Further, with recent advances in computers and communication technology, digital systems and color-image output systems have been applied also to the image-forming apparatus.

Electrophotographic imaging members (such as photoreceptors) are known, Electrophotographic imaging members are commonly used in electrophotographic processes having either a flexible belt or a rigid drum configuration, These electrophotogtaphic imaging members sometimes comprise a photoconductive layer including a single layer or composite layers. These electrophotographic imaging members take many different forms. For example, layered photoresponsive imaging members are known in the art. U.S. Pat. No. 4,265,990 to Stolka et al. describes a layered photoreceptor having separate photogenerating and charge-transport layers. The photogenerating layer disclosed in Stolka is capable of photogenerating holes and injecting the photogenerated holes into the charge-transport layer. Thus, in the photoreceptors of Stolka, the photogenerating material generates electrons and holes when subjected to light.

More advanced photoconductive photoreceptors containing highly specialized component layers are also known. For example, a multi-layered photoreceptor employed in electrophotograpilic imaging systems sometimes includes one or more of a substrate, an undercoating layer, an intermediate layer, an optional hole- or charge-blocking layer, a charge-generating layer (including a photogenerating material in a binder) over an undercoating layer and/or a blocking layer, and a charge-transport layer (including a charge-transport material in a binder). Additional layers such as one or more overcoat layer or layers are also sometimes included.

In view of such a background, improvement in electrophotographic properties and durability, miniaturization, reduction in cost, and the like, in electrophotographic photoreceptors have been studied, and electrophotographic photoreceptors using various materials have been proposed.

Production of a number of arylamine compounds, such as arylamine compounds that are useful as charge-transport compounds in electrostatographic imaging devices and processes, often involves synthesis of intermediate materials, some of which generally are costly and/or time-consuming to produce, and some of which involve a multi-step process.

One such class of intermediate products are disubstituted 4-aminobiphenyl compounds, which are themselves useful as a charge-transport compound in electrostatographic imaging devices and processes. Even production of this intermediate compound currently involves a long, costly process, which can include environmental and health risks.

Currently, such arylamine-derivative hole-transporting molecules are prepared by a process that includes a Knoevenagel reaction. See, for example, commonly assigned, U.S. patent application Ser. No. 10/992,687 filed Nov. 22, 2004. That process uses a catalyst in a solvent, and preferably uses the catalyst piperidine in toluene as a solvent. The use of the toluene was mainly to allow azeotropic distillation of the water byproduct formed during the reaction; however, the toluene itself was ineffective as a solvent. Accordingly, a large excess of the liquid catalyst piperidine was used to help with the dissolution of reactants. While this scheme is useful in small-scale reactions, the use of piperidine poses handling problems at large scale due to its toxicity and its flammability. Another concern related to the use of piperidine at large scale is the exotherm which occurs upon its addition.

Accordingly, improved processes providing safe, cost-effective and efficient methods for arylamine production are desired.

SUMMARY

The present disclosure addresses these and other needs, by providing a method for the preparation of an arylamine compound where the arylamine compound is a symmetric derivative of 4-aminobiphenyl or a triarylamine. More particularly this disclosure provides a method whereby a derivative of 4-aminobiphenyl or a triarylamine, such as a symmetric arylamine derivative of 4-aminobiphenyl, can be made using an improved Knoevenagel reaction followed by direct hydrogenation of a precursor organic salt, rather than a longer multi-step synthesis procedure. The improved Knoevenagel reaction uses a solid organic catalyst, rather than a liquid catalyst such as piperidine.

The arylamine derivative of 4-aminobiphenyl is further useful as an intermediate, which could be saponified to produce a dicarboxylic acid salt of an alkali earth compound. This dicarboxylic acid salt of an alkali earth compound can be further derivatized with an alkylhalide compound containing a siloxane moiety to produce a siloxane containing alylamine compound which is useful in the preparation of siloxane containing charge transporting layers for electrophotographic application.

In embodiments, the disclosure provides a process for converting an arylamine into an arylamine derivative, comprising:
 (i) providing a first arylamine compound;
 (ii) formylating said first arylamine compound to form a formyl substituted arylamine compound, where the first arylamine compound is not a formyl substituted arylamine compound; and
 (iii) acidifying said formyl substituted arylamine compound, in the presence of a solvent and a solid organic catalyst, to convert formyl functional groups into acid functional groups to form an acidified compound;
 wherein there is provided a second arylamine compound that is different from the first arylamine compound.

In other embodiments, the disclosure provides a process for forming a 4-aminobiphenyl derivative arylamine compound, comprising:
 (i) providing a first disubstituted 4-aminobiphenyl compound;
 (ii) formylating said first disubstituted 4-aminobiphenyl compound to form a bisformyl substituted compound, where said first disubstituted 4-aminzobiphenyl compound is not a bisformyl substituted compound; and
 (iii) acidifying said bisformyl substituted compound, in the presence of a solvent and a solid organic catalyst, to convert formyl functional groups into acid functional groups to form an acidified compound;
 wherein there is provided a second disubstituted 4-aminobiphenyl compound.

EMBODIMENTS

Figure 1:
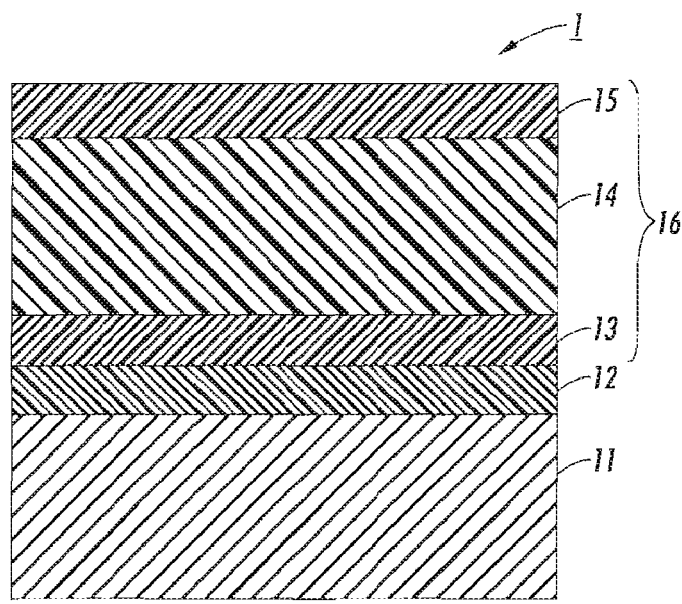
FIG. 1 is a schematic cross sectional view showing an embodiment of an electrophotographic photoreceptor of the disclosure.

This disclosure is not limited to particular embodiments described herein, and some components and processes may be varied by one of skill, based on this disclosure. The terminology used herein is for the purpose of describing particular embodiments only, and is not intended to be limiting.

In this specification and the claims that follow, singular forms such as "a," "an," and "the" include plural forms unless the content clearly dictates otherwise. In addition, reference may be made to a number of terms that shall be defined as follows:

The terms "hydrocarbon" and "alkane" refer, for example, to branched and unbranched molecules having the general formula $C_nH_{2n+2}$, wherein n is for example from 1 to about 100 or more such as methane, ethane, n-propane, isopropane, n-butane, isobutane, tert-butane, octane, decane, tetradecane, hexadecane, eicosane, tetracosane and the like. Alkanes may be substituted by replacing hydrogen atoms with one or more functional groups. The term "aliphatic" refers, for example, to straight-chain molecules, and may be used to describe acyclic, unbranched alkanes. The term "long-chain" refers, for example, to hydrocarbon chains in which n is a number of from about 8 to about 60, such as from about 20 to about 45 or from about 30 to about 40. The term "short-chain" refers, for example, to hydrocarbon chains in which n is an integer of from about 1 to about 7, such as from about 2 to about 5 or from about 3 to about 4.

The term "alkyl" refers, for example, to a branched or unbranched saturated hydrocarbon group, derived from an alkane and having the general formula $C_nH_{2n+1}$, wherein n is for example from 1 to about 100 or more such as methyl, ethyl, n-propyl, isopropyl, n-butyl, isobutyl, tert-butyl, octyl, decyl, tetradecyl, hexadecyl, eicosyl, tetracosyl and the like. The term "lower alkyl" refers, for example, to an alkyl group of from about 1 to about 12 carbon atoms. "Halogenated alkyl" refers, for example, to an alkyl group in which at least one hydrogen atom, and optionally all hydrogen atoms, is replaced by a halogen atom.

The term "aryl" refers, for example, to aromatic species of about 6 to about 20 carbon atoms or more, such as phenyl, naphthyl, anthrycyl, and the like. Optionally, these groups may be substituted with one or more independently selected substituents, including alkyl, alkenyl, alkoxy, hydroxyl and nitro groups.

The term "arylamine" refers, for example, to moieties containing both aryl and amine groups. Exemplary aralkylene groups have the structure Ar—NRR', in which Ar represents an aryl group and R and R' are groups that may be independently selected from hydrogen and substituted and unsubstituted alkyl, alkenyl, aryl and other suitable functional groups. The term "triarylamine" refers, for example, to arylamine compounds having the general structure NArAr'Ar", in which Ar, Ar' and Ar" represent independently selected aryl groups.

The term "organic molecule" refers, for example, to any molecule that is made up predominantly of carbon and hydrogen, such as, for example, alkanes and arylamines. The term "heteroatom" refers, for example, to any atom other than carbon and hydrogen. Typical heteroatoms included in organic molecules include oxygen, nitrogen, sulfur and the like.

"Alcohol" refers, for example, to an alkyl moiety in which one or more of the hydrogen atoms has been replaced by an —OH group. The term "lower alcohol" refers, for example, to an alkyl group of about 1 to about 6 carbon atoms in which at least one, and optionally all, of the hydrogen atoms has been replaced by an —OH group.

"Amine" refers, for example, to an alkyl moiety in which one or more of the hydrogen atoms has been replaced by an —$NH_2$ group. The term "lower amine" refers, for example, to an alkyl group of about 1 to about 6 carbon atoms in winch at least one, and optionally all, of the hydrogen atoms has been replaced by an —$NH_2$ group.

"Carbonyl compound" refers, for example, to an organic compound containing a carbonyl group, C=O, such as, for example, aldehydes, which have the general formula RCOH; ketones, which have the general formula RCOR'; carboxylic acids, which have the general formula RCOOH; and esters, which have the general formula RCOOR'.

The term "derivative" refers, for example, to compounds that are derived from another compound and maintain the same general structure as the compound from which they are derived. For example, saturated alcohols and saturated amines are derivatives of alkanes.

The term "homologous" refers, for example, to any number of series of organic compounds that have similar chemical properties and that differ by a constant relative molecular mass. For example, lower alcohols are a homologous series that includes $CH_3OH$, $CH_3CH_2OH$, $CH_3CH_2CH_2OH$, $CH_3(CH_2)_2CH_2OH$, $CH_3(CH_2)_3CH_2OH$ and $CH_3(CH_2)_4CH_2OH$, as well as isomers of these molecules.

The term "saturated" refers, for example, to compounds containing only single bonds. The term "unsaturated" refers, for example, to compounds that contain one or more double bonds and/or one or more triple bonds.

The term "reflux" refers, for example, to the process of boiling a liquid, condensing the vapor and returning the vapor to the original container. When a liquid is refluxed, the temperature of the boiling liquid remains constant. The term "boiling point" refers, for example, to the temperature at which the saturated vapor pressure of a liquid is equal to the external atmospheric pressure.

The terms "standard temperature" and "standard pressure" refer, for example, to the standard conditions used as a basis where properties vary with temperature and/or pressure. Standard temperature is 0° C.; standard pressure is 101,325 Pa or 760.0 mmHg. The term "room temperature" refers, for example, to temperatures in a range of from about 20° C. to about 25° C.

The terms "high temperature environment" and "high temperature conditions" refer, for example, to an atmosphere in which the temperature is at least about 28 or about 30° C., and may be as high as about 300° C. The terms "high humidity environment" and "high humidity conditions" refer, for example, to an atmosphere in which the relative humidity is at least about 75 or about 80%.

The terms "one or more" and "at least one" herein mean that the description includes instances in which one of the subsequently described circumstances occurs, and that the description includes instances in which more than one of the subsequently described circumstances occurs.

A process for producing derivatives of triarylamines and 4-aminobiphenyl and similar compounds is to utilize a Knoevenagel reaction with a solid organic catalyst and a suitable solvent, followed by an optional direct hydrogenation reaction on an organic salt. In the case of forming derivatives of 4-aminobiphenyl, the process converts a first disubstituted 4-aminobiphenyl compound into a second, different disubstituted 4-aminobiphenyl compound.

The starting compound can be any suitable arylamine compound that is to be subsequently subjected to a Knoevenagel reaction to form a second, different arylamine compound. For example, suitable arylamines include compounds of the formula:

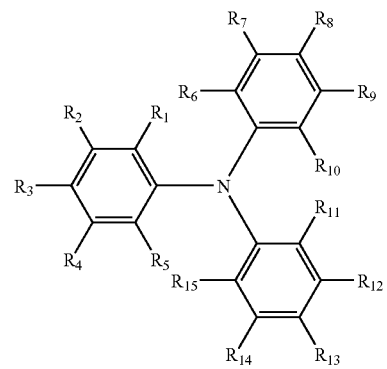

where $R^1$-$R^{15}$, which can be the same or different, can be suitably selected to represent hydrogen, a halogen, an alkyl group having for example from 1 to about 20 carbon atoms, an aryl group optionally substituted by one or more alkyl groups, an alkyl group containing a heteroatom, an aryl group containing a heteroatom and optionally substituted by one or more alkyl groups, and the like. In embodiments, the arylamine is a triarylamine. In other embodiments, the arylamine is a diphenylamine derivative, such as a disubstituted 4-aminobiphenyl compound of the formula

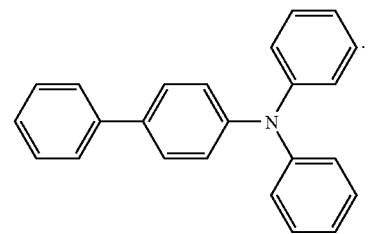

In a first process step, a suitable arylamine such as a disubstituted aminophenyl compound or a disubstituted 4-aminobiphenyl compound, is formylated by means of a Vilsmeier (or Vilsmeier-Haack) reaction, to form a bisformyl substituted compound. Those skilled in the art will recognize there may be other ways and methods for the introduction of a formyl group into a compound of this type, for example by treatment of a halogenated derivative of the arylamine compound with n-butyllithium followed by dimethylformamide (DMF) or treatment of such a compound with hexamethylene tetraamine in the presence of trifluoroacetic acid. One suitable method for forming bisformyl substituted compounds is disclosed in U.S. patent application Ser. No. 10/909,136 filed Jul. 30, 2004, the entire disclosure of which is incorporated herein by reference. Accordingly, neither the Vilsmeier (or Vilsmeier-Haack) reaction nor the n-butyllithium treatment nor the hexamethylene tetraamine treatment is meant to be an exhaustive list.

Suitable examples of the starting arylamine compound, such as a first disubstituted aminophenyl compound or a first disubstituted 4-aminobiphenyl compound, include, for example, compounds of the following general formulas:

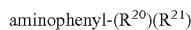

aminophenyl-$(R^{20})(R^{21})$

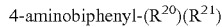

4-aminobiphenyl-$(R^{20})(R^{21})$ where $R^{20}$ and $R^{21}$, which can be the same or different and represent aromatic or heterocyclic groups. Suitable aromatic groups include, for example, substituted or unsudstituted phenyl groups; substituted or unsubstituted groups including two or more phenyl groups, such as biphenyl groups, triphenyl groups, and the like; substituted or unsubstituted fused polycyclic hydrocarbons, for example having from 2 to about 10 fused benzene rings, such as naphthyl groups, anthryl groups, phenanthryl groups, pyrenyl groups, and the like; and mixtures thereof. Suitable heterocyclic groups include, for example, substituted or unsubstituted 3- to 10-membered rings (preferably 5- or 6-membered rings) containing one or more heteroatoms, such as oxygen, sulfur, selenium, tellurium, nitrogen, phosphorus, arsenic, antimony, bismuth, silicon, germanium, tin, lead and mercury. Examples of such heterocyclic groups include, for example, substituted or unsubstituted groups selected from thiophene, pyridine, diazine, triazine, and the like. Substitution of these groups can be at one or more locations on the aromatic or heterocyclic ring(s), and can be by, for example, an alkyl groups of from 1 to about 15 carbon atoms, an alkenyl groups of from 1 to about 15 carbon atoms, alkynyl groups of from 1 to about 15 carbon atoms, halogen atoms, acid groups, ester groups, and the like. It will be appreciated by those skilled in the art that other compounds can also be used to provide a desired arylamine, and the invention is not limited to the above-listed compounds.

The starting arylamine such as the first disubstituted aminophenyl compound or the first disubstituted 4-aminobiphenyl compound is subjected to a Vilsmeier reaction, to form a bisformyl substituted compound. Such formylation reactions are generally well known in the art, and thus are not described in detail herein. For example, N,N-diphenyl-4-aminobiphenyl can be formylated (bisformylated) by reacting the compound with dimethylformamide (DMF) and phosphorus oxychloride ($POCl_3$). The result of the formylation step is a compound of the following general formula:

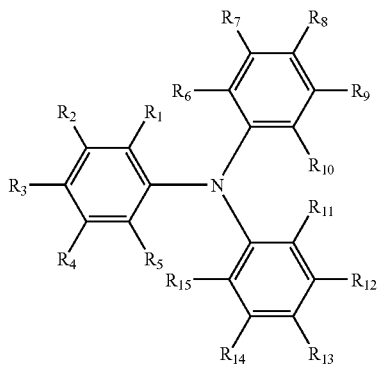

wherein $R^1$-$R^{15}$ are defined above, but where at least one or more of the $R^1$-$R^{15}$ groups is formylated to include a terminal —CH=O group. In embodiments, at least one group on at least two different phenyl rings, such as the $R^8$ and $R^{13}$ groups, is formylated to include a terminal —CH=O group. In another embodiment, at least one group on at least three different phenyl rings, such as the $R^3$, $R^8$, and $R^{13}$ groups, is formylated to include a terminal —CH=O group. Thus, for example, at least one of the $R^6$-$R^{10}$ groups and at least one of the $R^{11}$-$R^{15}$ groups are formylated to include a terminal —CH=O group. In the case where the starting arylamine is a first disubstituted 4-aminobiphenyl compound of the formula 4-aminobiphenyl-$(R^{20})(R^{21})$, the resultant formylated compound is a compound of the formula:

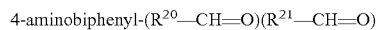

4-aminobiphenyl-$(R^{20}$—CH=O$)(R^{21}$—CH=O$)$ where $R^{20}$ and $R^{21}$ are as described above, except that the groups have been substituted with a —CH=O group.

Of course, it will be recognized by those skilled in the art that the formylating reaction step can be omitted, where the starting arylamine compound such as a first disubstituted 4-aminobiphenyl compound is already a bisformyl substituted compound. Thus, the formylating step is optional in those embodiments where the starting material is a formylated compound, but may be necessary where the starting material is not a formylated compound.

In a second step, the bisformylated compound of the first step is subjected to a condensation or modification reaction, to convert the formyl end groups into acid groups. For example, the bisformylated compound of the first step can be subjected to a Knoevenagel condensation reaction, or specifically to a Doebner modification condensation reaction, to convert the —CH=O formyl end groups into —C=C—COOH carboxylic acid end groups. In embodiments, the Knoevenagel condensation reaction can be conducted by reaction of the formylated, such as bisformylated, compound with an active methylene compound in the presence of a suitable catalyst and a suitable solvent.

Such Knoevenagel condensation reactions are also generally known in the art, and thus are not described in detail herein. However, for a brief explanation, the Knoevenagel reaction generally involves the condensation of an aldehyde with malonic acid, catalyzed by a weak base, such as by the following reaction:

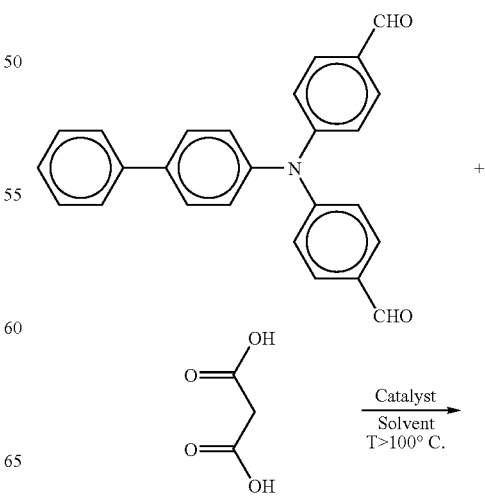

-continued

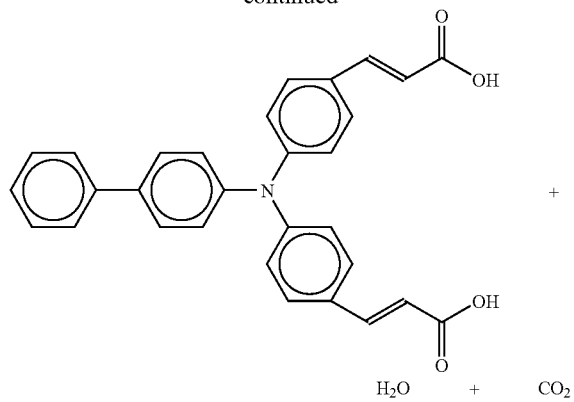

The reaction byproducts are water and, under elevated temperature, carbon dioxide. Azeotropic removal of water is often necessary to drive the reaction to completion. A suitable solvent (such as toluene) is often employed to meet these requirements, although the toluene typically only helps in the azeotropic removal of water. The Doebner modification, which utilizes refluxing pyridine as both solvent and catalyst, is also a suitable method for use. Another frequently used solvent is piperidine. In fact, some existing processes tend to use large amounts of the liquid catalyst such as piperidine, so that the material acts as both a catalyst and as a solvent for the reactants. In this manner, however, the excess piperidine helps to dissolve the reactants, but it also reacts with the carboxylic acid of the product to form a piperidine salt, such as of the following formula:

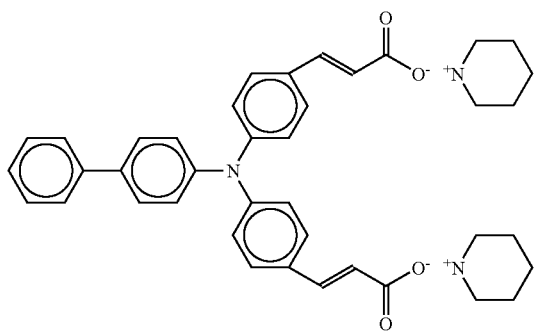

The salt is generally insoluble in the solvent system and exists as a sticky solid that presents difficulties in handling. Acid treatment is thus generally required to break the salt bond.

However, an aspect of embodiments is that the catalyst and solvent are specifically selected to provide desired results. In particular, the catalyst is selected to be a solid catalyst, rather than a liquid catalyst such as piperidine or pyridine. Solid catalysts are selected over liquid catalyst, in view of the general toxicity and flammability of the common liquid catalysts. Likewise, the solvent is specifically selected in combination with the selected catalyst, to provide a reaction that proceeds quickly, or at least comparably to the reaction using piperidine or pyridine and toluene, that has acceptably high yield, and that is scaleable for product handling.

In embodiments, suitable solid organic catalysts are weak bases that include, for example, amines and amine salts such as piperazine, piperidinium acetate, dimethylaminopyridine, ammonium acetate, amino acids (such as β-alanine) and the like. See, for example, A. R. Khosropour, et al., J. Chem. Res., 6, 364-365 (2005), and F. S. Prout, et al., J. Chem. Eng. Data, 8(4), 597-599 (1963), the entire disclosure of which are incorporated herein by reference.

In embodiments, suitable solvents include those solvents that solubilize the reaction components, particularly the reactants, and more particularly the solid organic catalyst. Thus, for example, toluene is not a suitable solvent because it does not solubilize the malonic acid, and particularly because it does not solubilize the solid catalyst. In embodiments, it is also desired that the solvent does not also function as a catalyst for the reaction. Thus, for example, pyridine, dimethylpyridine, and piperidine are not desirably used. Suitable solvents that can be used thus include, for example, dimethylformamide (DMF), and the like. Triethanolamine can also be used as a solvent; however, it is generally highly viscous and more difficult to remove. However, some otherwise unsuitable solvents, such as toluene, can be used in combination with another suitable solvent. Thus, for example, a combination of dimethylformamide and toluene can be used, in embodiments.

Any suitable active methylene compound can be used in the reaction. In embodiments, a particularly suitable active methylene compound is a malonic acid or ester, such as malonic acid. Other suitable active methylene compounds include, for example, malonamides, malononitrile, cyanoacetic acid, cyanoacetic esters, cyanoacetamides, and the like.

Although the resultant acidified compound can be isolated from the reactants and solvent following completion of the reaction, such separation is not required. Thus, for example, in some embodiments the reaction product mixture of the second step can be used directly in the succeeding optional third step, described below, without purification or isolation.

The Knoevenagel reaction can be conducted at any suitable temperature, although an elevated temperature is desired in embodiments. In particular, because toluene is not used for the azeotropic removal of water, the reaction can be conducted at higher temperatures than previously used. In embodiments, the reaction is conducted at a temperature of about 50° C. to about 300° C., such as about 75° C. to about 250° C. or about 100° C. to about 200° C.

In an optional third step, a hydrogenation reaction can be used to directly and mildly hydrogenate unsaturated double bonds produced in the second step. Such direct hydrogenation can be conducted in the presence of a suitable catalyst, such as a rhodium, palladium, platinum, raney nickel, or the like catalyst. The catalyst can be supported on a substrate, such as a carbon substrate, if desired. In embodiments, a 10% palladium on wet carbon catalyst is preferred.

The result of the process of the present disclosure is the formation of a desired arylamine compound, which can broadly be characterized as a dicarboxylic acid arylamine. For example, where the starting arylamine is a disubstituted 4-aminobiphenyl, the resultant compound can broadly be characterized as a derivative of 4-aminobiphenyl. Thus, for example, the arylamine compounds provided by the present invention can be represented by the following general formula:

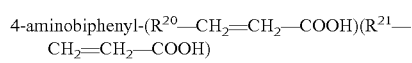

where $R^{20}$ and $R^{21}$, which can be the same or different, are as described above. If the product is optionally hydrogenated, as described above, then the product can be represented by the following general formula:

4-aminobiphenyl-$(R^{20}$—$CH_2$—$CH_2$—COO—$X1^+)$
$(R^{21}$—$CH_2$—$CH_2$—COO—$X_2^+)$ where $R^{20}$ and $R^{21}$, which can be the same or different, are as described above, and $X_1$ and $X_2$, which can be the same or different, are cationic groups, such as hydrogen ions ($H^+$), potassium ions ($K^+$), or the like.

After each step in the process, suitable separation, filtration, and purification processes can be conducted, as desired. For example, after the third step, the final product can be isolated, for example, by a suitable recrystallization procedure. All of these procedures are conventional and will be apparent to those skilled in the art.

The improved Knoevenagel reaction of the present disclosure provides significant and distinct advantages over current arylamine production processes. These advantages, which are provided by selection of a solid catalyst and improved solvent for the reaction, include process improvements, and environmental and health benefits. These advantages and benefits include one or more of the following:

Absence of Exotherm—In the current method that utilizes toluene and piperidine catalyst, the addition of piperidine must be done slowly in order to control a large exotherm or generation of heat. Although exotherms are acceptable and can be accommodated in laboratory-scale processes, reactive exotherms are generally undesired and to be avoided at large scale processes, where the exotherm can result in excessive heat generation that can affect the process, equipment, plant, and the like. However, in the present selection of a solid catalyst and an improved solvent such as DMF, the catalyst can be added all at once, as there is no significant exotherm. This results in an improved process because all of the catalyst is present at once, and without a generated exotherm that hinders or complicates scale-up. In embodiments, the Knoevenagel reaction proceeds without an appreciable exotherm, such as with no exotherm at all, or an exotherm of less than about 10° C.

Homogeneous Mixture—In a toluene solvent system, solid catalysts of the present disclosure are not soluble. However, with an improved solvent such as DMF, a solid organic catalyst may be used as it is easily dissolved into a single phase. This results in a homogeneous mixture throughout the reaction, presenting clear mixing advantages.

Unnecessary Azeotropic Distillation—The Knoevenagel reaction produces water as a reaction byproduct. Water is desirably removed as it is produced, such as via an azeotropic distillation, in order to drive the reaction to completion. In current processes that utilize toluene as a solvent, the water removal limits the reaction temperature to that of the toluene-water reflux temperature. In contrast, improved processes of the disclosure using an improved solvent and a solid organic catalyst system, obviates the need for such a distillation in order for the reaction to progress. That is, water does not need to be removed No azeotropic distillation for the removal of water thus widens the reaction temperature window, allowing faster reaction times.

Ease of Product Work Up—Once the reaction is complete, the product can be isolated by precipitation in water. In the current toluene-piperidine method, the reaction product is present as a piperidine salt, which salt must be broken by addition of sulfuric acid. The initial precipitation of the reaction products into the water and sulfuric acid solution results in a sticky solid that is very difficult to mix, and requires many acid washes in order to isolate the product. Also, because the toluene-piperidine reaction is a 2-phase system, some reaction product will be trapped in the toluene phase and can be difficult to extract. In contrast, the improved solvent and solid organic catalyst system precipitates cleanly into water, producing an easy to handle powdery solid, requiring only water washes to remove trace solvent.

Health and Safety Advantages—The improved solvent used in place of toluene also provides health and safety advantages. For example, such solvents as DMF enable the dissolution of all reagents and organic catalysts, creating a homogenous mixture, which was not possible using toluene. This allows the use of safer, less toxic solid catalysts which were less effective in a toluene-based solvent system. For example, piperidine and toluene are the conventional choices for the Knoevenagel reaction mixture. As shown in the table below, piperidine rates poorly in the categories of both Health and Flammability (3/3). However, with the use of DMF as a solvent, additional catalysts can be used in the reaction, all posing less of a health and safety risk than piperidine. For example, the suitable solid catalysts piperazine (3/0) offers an advantage due to a higher flash point, and ammonium acetate (0/0) and β-alanine (0/0) are not considered to pose any Health and Safety risk whatsoever.

| | HMIS/NFPA Ratings for various catalysts | | | |
|---|---|---|---|---|
| | Health | Flammability | Flash Point (° C.) | Reactivity |
| Piperidine | 3 | 3 | 16 | 1 |
| Piperazine | 3 * | 0 | 82 | 1 |
| Ammonium acetate | 0 | 0 | N/A | 0 |
| β-alanine | 0 | 0 | N/A | 0 |

* additional chronic hazards

The choice of DMF (2/2) over toluene (2/3) as the solvent system itself presents a Health and Safety advantage due to the higher flashpoint of DMF. The table below outlines the health and safety ratings of these and several other solvents that may offer potential advantages to the Knoevenagel reaction.

| | HMIS/NFPA Ratings for various solvents | | | |
|---|---|---|---|---|
| | Health | Flammability | Flash Point (° C.) | Reactivity |
| Toluene | 2 * | 3 | 4 | 0 |
| Pyridine | 2 * | 3 | 17 | 0 |
| Lutidine | 2 | 3 | 37-50 | 0 |
| DMF | 2 * | 2 | 57.78 | 0 |

* additional chronic hazards

The arylamine produced by this process can itself be used as a final product, or it can be further processed and/or reacted to provide other compounds for their separate use. For example, the arylamine can be used itself as a charge-transport material in an electrostatographic imaging member, or it can be further processed and/or reacted to provide other charge-transport materials or other compounds useful in such electrostatographic imaging member. An exemplary electrostatographic imaging member will now be described in greater detail.

In electrophotographic photoreceptors of embodiments, the photoreceptors can include various layers such as undercoating layers, charge generating layers, charge transport layers, overcoat layers, and the like. The overcoating layers of embodiments can be a silicon overcoat layer, which can comprise one or more silicon compounds, a resin, and a charge transport molecule such as an arylamine.

In embodiments, the resin may be a resin soluble in a liquid component in a coating solution used for formation of a silicon overcoat layer. Such a resin soluble in the liquid component may be selected based upon the kind of liquid component. For example, if the coating solution contains an alcoholic solvent, a polyvinyl acetal resin such as a polyvinyl butyral resin, a polyvinyl formal resin or a partially acetalized polyvinyl acetal resin in which butyral is partially modified with formal or acetoacetal, a polyamide resin, a cellulose resin such as ethyl cellulose and a phenol resin may be suitably chosen as the alcohol-soluble resins. These resins may be used either alone or as a combination of two or more resins. Of the above-mentioned resins, the polyvinyl acetal resin is particularly suitable in embodiments in terms of electric characteristics.

In embodiments, the weight-average molecular weight of the resin soluble in the liquid component may be from about 2,000 to about 1,000,000, such as from about 5,000 to about 50,000. When the weight-average molecular weight is less than about 2,000, enhancing discharge gas resistance, mechanical strength, scratch resistance, particle dispersibility, etc., tend to become insufficient. However, when the weight-average molecular weight exceeds about 1,000,000, the resin solubility in the coating solution decreases, and the amount of resin added to the coating solution may be limited and poor film formation in the production of the photosensitive layer may result.

Further, the amount of the resin soluble in the liquid component may be, in embodiments, from about 0.1 to about 15% by weight, or from about 0.5 to about 10% by weight, based on the total amount of the coating solution. When the amount added is less than 0.1% by weight, enhancing discharge gas resistance, mechanical strength, scratch resistance, particle dispersibility, etc. tend to become insufficient. However, if the amount of the resin soluble in the liquid component exceeds about 15% by weight, there is a tendency for formation of indistinct images when the electrophotographic photoreceptor of the disclosure is used at high temperature and high humidity.

There is no particular limitation on the silicon compound used in embodiments of the disclosure, as long as it has at least one silicon atom. However, a compound having two or more silicon atoms in its molecule may be used in embodiments. The use of the compound having two or more silicon atoms in its molecule allows both the strength and image quality of the electrophotographic photoreceptor to be achieved at higher levels.

Further, in embodiments, the silicon compounds may include silane coupling agents such as a tetrafunctional alkoxysilane, such as tetramethoxysilane, tetraethoxysilane and the like; a trifunctional alkoxysilane such as methyltrimethoxy-silane, methyltriethoxysilane, ethyl trimethoxysilane, methyltrimethoxyethoxysilane, vinyltrimethoxysilane, vinyltriethoxysi lane, phenyltrimethoxysilane, γ-glycidoxypropylmethyldiethoxysilane, γ-glycidoxypropyltrimethoxysilane, γ-glycidoxypropyl-triethoxysilanie, γ-aminopropyltriethoxysilane, γ-aminopropyltrimethoxysilane, γ-aminopropylmethyldimethoxysilane, N-β-(aminoethyl)-γ-aminopropyltriethoxysilane, (tridecafluoro-1,1,2,2-tetrahydrooctyl)triethoxysilane, (3,3,3-trifluoropropyl)-trimethoxysilane, 3-(heptafluoroisopropoxy)propyltriethoxysilane, 1H,1H,2H,2H-perfluoroalkyltriethoxysilane, 1H,1H,2H2H-perfluorodecyltriethoxysilane or 1H,1H,2H,2H-perfluorooctyltrietlhoxysilane; a bifunctional alkoxysilane such as dimethyldimethoxysilane, diphenyldimethoxysilane or methylphenyldimethoxysilane; and a monofunctional alkoxysilane such as trimethylmethoxysilane. In order to improve the strength of the photosensitive layer, trifunctional alkoxysiuanes and tetrafunctional alkoxysilanes may be used in embodiments, and in order to improve the flexibility and film forming properties, monofunctional alkoxysilanes and bifunctional alkoxysilanes may be used in embodiments.

Silicone hard coating agents containing these coupling agents can also be used in embodiments. Commercially available hard coating agents include KP-85, X-40-9740 and X-40-2239 (available from Shinetsu Silicone Co., Ltd.), and AY42-440, AY42-441 and AY49-208 (available from Toray Dow Corning Co., Ltd.).

Various fine particles can also be added to the silicon compound-containing layer. The fine particles may be used either alone or as a combination of two or more such fine particles. Non-limiting examples of the fine particles include fine particles containing silicon, such as fine particles containing silicon as a constituent element, and specifically include colloidal silica and fine silicone particles.

Colloidal silica used in embodiments as the fine particles containing silicon in the disclosure is selected from an acidic or alkaline aqueous dispersion of the fine particles having an average particle size of 1 to 100 nn, or 10 to 30 nm, and a dispersion of the fine particles in an organic solvent such as an alcohol, a ketone or an ester, and generally, commercially available particles can be used.

There is no particular limitation on the solid content of colloidal silica in a top surface layer of the electrophotographic photoreceptor of embodiments. However, in embodiments, colloidal silica may be included in amounts of from about 1 to about 50% by weight, such as from about 5 to about 30% by weight, based on the total solid content of the top surface layer, in terms of film forming properties, electric characteristics and strength.

The fine silicone particles used as the fine particles containing silicon in the disclosure are selected from silicone resin particles, silicone rubber particles and silica particles surface-treated with silicone, which are spherical and have an average particle size of from about 1 to 500 nm, such as from about 10 to about 100 nm, and generally, commercially available particles can be used in embodiments.

In embodiments, the fine silicone particles are small-sized particles that are chemically inactive and excellent in dispersibility in a resin, and further are low in content as may be necessary for obtaining sufficient characteristics. Accordingly, the surface properties of the electrophotographic photoreceptor can be improved without inhibition of the crosslinking reaction. That is to say, fine silicone particles improve the lubricity and water repellency of surfaces of electrophotographic photoreceptors where incorporated into strong crosslinked structures, which may then be able to maintain good wear resistance and stain adhesion resistance for a long period of time. The content of the fine silicone particles in the silicon compound-containing layer of embodiments may be from about 0.1 to about 20% by weight, such as from about 0.5 to about 10% by weight, based on the total solid content of the silicon compound-containing layer.

Other fine particles that may be used in embodiments include fine fluorine-based particles such as ethylene tetrafluoride, ethylene trifluoride, propylene hexafluoride, vinyl fluoride and vinylidene fluoride, and semiconductive metal oxides such as $ZnO$—$Al_2O_3$, $SnO_2$—$Sb_2O_3$, $In_2O_3$—$SnO_2$, $ZnO$—$TiO_2$, $MgO$—$Al_2O_3$, $FeO$—$TiO_2$, $TiO_2$, $SnO_2$, $In_2O_3$, $ZnO$ and $MgO$.

In conventional electrophotographic photoreceptors, when the above-mentioned fine particles are contained in the photosensitive layer, the compatibility of the fine particles with a charge transport substance or a binding resin may become insufficient, which causes layer separation in the photosensitive layer, and thus the formation of an opaque film. As a result, the electric characteristics have deteriorated in some cases. In contrast, the silicon compound-containing layer of embodiments (a charge transport layer in this case) may contain the resin soluble in the liquid component in the coating solution used for formation of this layer and the silicon compound, thereby improving the dispersibility of the fine particles in the silicon compound-containing layer. Accordingly, the pot life of the coating solution can be sufficiently prolonged, and it becomes possible to prevent deterioration of the electric characteristics.

Further, an additive such as a plasticizer, a surface modifier, an antioxidant, or an agent for preventing deterioration by light can also be used in the silicon compound-containing layer of embodiments. Non-limiting examples of plasticizers that may be used in embodiments include, for example, biphenyl, biphenyl chloride, terphenyl, dibutyl phthalate, diethylene glycol phthalate, dioctyl phthalate, triphenylphosphoric acid, methylnaphthalene, benzophenotne, chlorinated paraffin, polypropylene, polystyrene and various fluorohydrocarbons.

The antioxidants may include an antioxidant having a hindered-phenol, hindered-amine, thioether or phosphite partial structure. This is effective for improvement of potential stability and image quality in environmental variation. The antioxidants include an antioxidant having a hindered-phenol, hindered-amine, thioether or phosphite partial structure. This is effective for improvement of potential stability and image quality in environmental variation. For example, the hindered-phenol antioxidants include SUMILIZER BHT-R, SUMILIZER MDP-S, SUMILIZER BBM-S, SUMILIZER WX-R, SUMILIZER NW, SUMILIZER BP-76, SUMILIZER BP-101, SUMILIZER GA-80, SUMILIZER GM and SUMILIZER GS (the above are manufactured by Sumitomo Chemical Co., Ltd.), IRGANOX 1010, IRGANOX 1035, IRGANOX 1076, IRGANOX 1098, IRGANOX 1135, IRGANOX 1141, IRGANOX 1222, IRGANOX 1330, IRGANOX 1425WLj, IRGANOX 1520Lj, IRGANOX 245, IRGANOX 259, IRGANOX 3114, IRGANOX 3790, IRGANOX 5057 and IRGANOX 565 (the above are manufactured by Ciba Specialty Chemicals), and ADECASTAB AO-20, ADECASTAB AO-30, ADECASTAB AO-40, ADECASTAB AO-50, ADECASTAB AO-60, ADECASTAB AO-70, ADECASTAB AO-80 and ADECASTAB AO-3301 (the above are manufactured by Asahi Denka Co., Ltd.). The hindered-amine antioxidants include SANOL LS2626, SANOL LS765, SANOL LS770, SANOL LS744, TINUVIN 144, TINUVIN 622LD, MARK LA57, MARK LA67, MARK LA62, MARK LA68, MARK LA63 and SUMILIZER TPS, and the phosphite antioxidants include MARK 2112, MARK PEP•8, MARK PEP•24G, MARK PEP•36, MARK 329K and MARK HP•10. Of these, the hindered-phenol and hindered-amine antioxidants may be particularly suitable, in embodiments.

There is no particular limitation on the thickness of the silicon-containing layer, however, in embodiments, the silicon-containing layer may be from about 2 to about 5 μm in thickness, such as from about 2.7 to about 3.2 μm in thickness.

The electrophotographlic photoreceptor of embodiments may be either a function-separation-type photoreceptor, in which a layer containing a charge-generation substance (charge-generation layer) and a layer containing a charge-transport substance (charge-transport layer) are separately provided, or a monolayer-type photoreceptor, in which both the charge-generation layer and the charge-transport layer are contained in the same layer, as long as the electrophotographic photoreceptor of the particular embodiment has the photosensitive layer provided with the above-mentioned silicon compound-containing layer. The electrophotographic photoreceptor will be described in greater detail below, taking the function-separation-type photoreceptor as an example.

FIG. 1 is a cross-sectional view schematically showing an embodiment of the electrophotographic photoreceptor of the disclosure. The electrophotographic photoreceptor 1 shown in FIG. 1 is a function-separation-type photoreceptor in which a charge-generation layer 13 and a charge-transport layer 14 are separately provided. That is, an underlayer 12, the charge-generation layer 13, the charge transport layer 14 and a protective layer 15 are laminated onto a conductive support 11 to form a photosensitive layer 16. The protective layer 15 contains a resin soluble in the liquid component contained in the coating solution used for formation of this layer and the silicon compound. The various layers of the photoreceptor shown in FIG. 1 are generally known, and are described in detail in the above-mentioned commonly owned and co-pending applications.

The electrophotographic photoreceptor of embodiments should not be construed as being limited to the above-mentioned constitution. For example, the electrophotographic photoreceptor shown in FIG. 1 is provided with the protective layer 15. However, when the charge transport layer 14 contains the resin soluble in the liquid component in the coating solution used for formation of this layer and the silicon compound, the charge transport layer 14 may be used as a top surface layer (a layer on the side farthest apart from the support 11) without using the protective layer 15. In this case, the charge-transport substance contained in the charge transport layer 14 is desirably soluble in the liquid component in the coating solution used for formation of the charge-transport layer 14. For example, when the coating solution used for formation of the charge-transport layer 14 contains an alcohol solvent, the silicon compounds described above, including arylamine derivatives prepared by processes that include selective hydrogenation by catalytic transfer, can be used as the charge-transport substances. In embodiments, a particularly suitable charge-transport molecule is the following arylamine, which may be produced from the arylamines described herein.

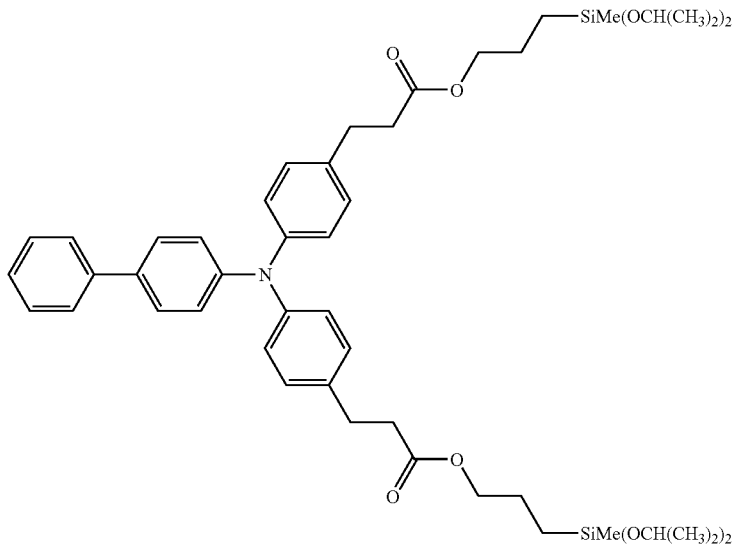

Figure 2:
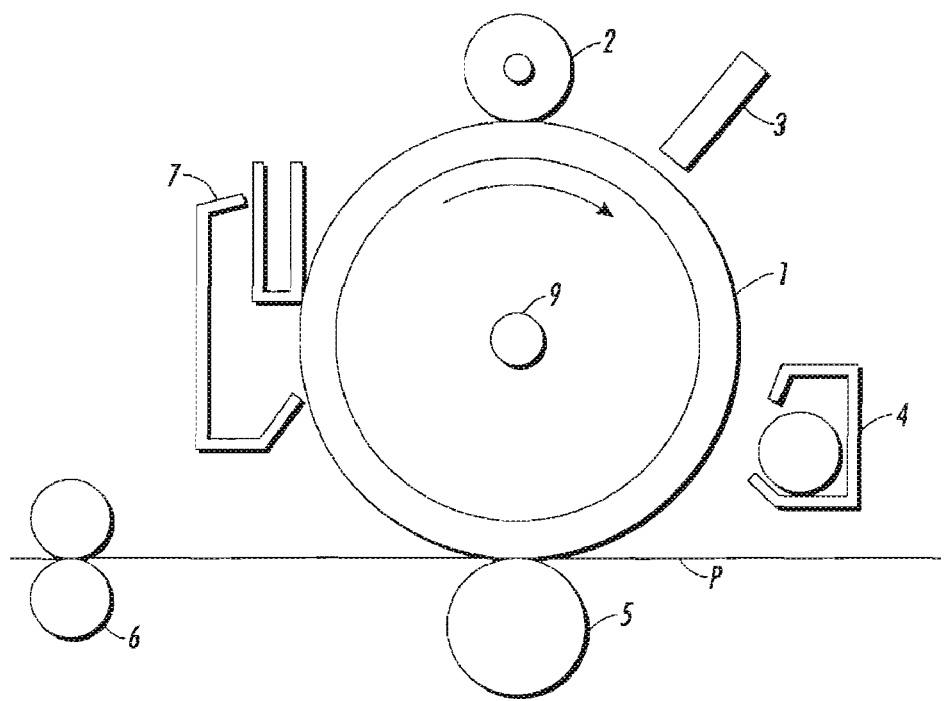
FIG. 2 is a schematic view showing an embodiment of an image-forming apparatus of the disclosure.

FIG. 2 is a schematic view showing an embodiment of an image forming apparatus or xerographic machine. In the apparatus shown in FIG. 2, an electrophotographic photoreceptor 1 is supported by a support 9, and rotatable at a specified rotational speed in the direction indicated by the arrow, centered on the support 9, A charging device 2, an exposure device 3, a developing device 4, a transfer device 5 and a cleaning unit 7 are arranged in this order along the rotational direction of the electrophotographic photoreceptor 1. Further, this exemplary apparatus is equipped with an image fixing device 6, and a medium P to which a toner image is to be transferred is conveyed to the image fixing device 6 through the transfer device 5.

Figure 3:
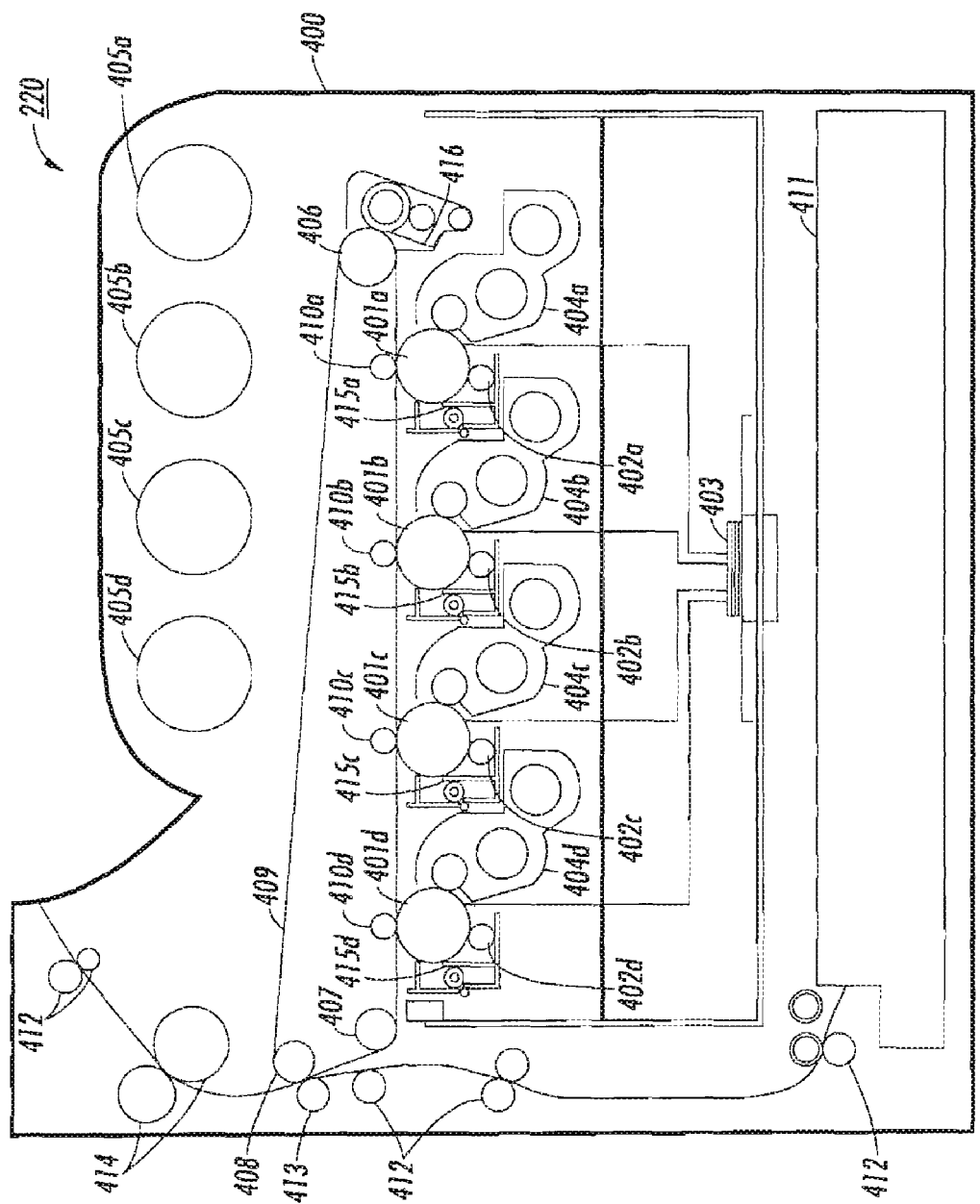
FIG. 3 is a schematic view showing another embodiment of an image-forming apparatus of the disclosure.

FIG. 3 is a cross-sectional view showing another exemplary embodiment of an image-forming apparatus. The image-forming apparatus 220 shown in FIG. 3 is an image-forming apparatus of an intermediate-transfer system, and four electrophotographic photoreceptors 401a to 401d are arranged in parallel with each other along an intermediate-transfer belt 409 in a housing 400.

Here, the electrophotographic photoreceptors 401a to 401d carried by the image-forming apparatus 220 are each the electrophotographic photoreceptors. Each of the electrophotographic photoreceptors 401a to 401d may rotate in a predetermined direction (counterclockwise on the sheet of FIG. 3), and charging rolls 402a to 402d, developing device 404a to 404d, primary transfer rolls 410a to 410d and cleaning blades 415a to 415d are each arranged along the rotational direction thereof. In each of the developing device 404a to 404d, four-color toners of yellow (Y), magenta (M), cyan (C) and black (B) contained in toner cartridges 405a to 405d can be supplied, and the primary transfer rolls 410a to 410d are each brought into abutting contact with the electrophotographic photoreceptors 401a to 401d through an intermediate transfer belt 409.

Further, a laser-light source (exposure unit) 403 is arranged at a specified position in the housing 400, and it is possible to irradiate surfaces of the electrophotographic photoreceptors 401a to 401d after charging with laser light emitted from the laser-light source 403. This performs the respective steps of charging, exposure, development, primary transfer and cleaning in turn in the rotation step of the electrophotographic photoreceptors 401a to 401d, and toner images of the respective colors are transferred onto the intermediate-transfer belt 409, one over the other.

The intermediate-transfer belt 409 is supported with a driving roll 406, a backup roll 408 and a tension roll 4037 at a specified tension, and rotatable by the rotation of these rolls without the occurrence of deflection. Further, a secondary transfer roll 413 is arranged so that it is brought into abutting contact with the backup roll 408 through the intermediate-transfer belt 409. The intermediate-transfer belt 409, which has passed between the backup roll 408 and the secondary transfer roll 413, is cleaned up by a cleaning blade 416, and then repeatedly subjected to the subsequent image-formation process.

Further, a tray (tray for a medium to which a toner image is to be transferred) 411 is provided at a specified position in the housing 400. The medium to which the toner image is to be transferred (such as paper) in the tray 411 is conveyed in turn between the intermediate-transfer belt 409 and the secondary transfer roll 413, and further between two fixing rolls 414 brought into abutting contact with each other, with a conveying roll 412, and then delivered out of the housing 400.

According to the exemplary image-forming apparatus 220 shown in FIG. 3, the use of electrophotographic photoreceptors of embodiments as electrophotographic photoreceptors 401a to 401d may achieve discharge gas resistance, mechanical strength, scratch resistance, etc. on a sufficiently high level in the image-formation process of each of the electrophotographic photoreceptors 401a to 401d. Accordingly, even when the photoreceptors are used together with the contact-charging devices or the cleaning blades, or further with the spherical toner obtained by chemical polymerization, good image quality can be obtained without the occurrence of image defects such as fogging. Therefore, also according to the image-forming apparatus for color image formation using the intermediate-transfer body, such as this embodiment, the image-forming apparatus, which can stably provide good image quality for a long period of time, is realized.

The disclosure should not be construed as being limited to the above-mentioned embodiments. For example, each apparatus shown in FIG. 2 or 3 may be equipped with a process cartridge comprising the electrophotographic photoreceptor 1 (or the electrophotographic photoreceptors 401a to 401d) and charging device 2 (or the charging devices 402a to 402d). The use of such a process cartridge allows maintenance to be performed more simply and easily.

Further, in embodiments, when a charging device of the non-contact charging system such as a corotron charger is used in place of the contact-charging device 2 (or the contact-charging devices 402a to 402d), sufficiently good image quality can be obtained.

Specific examples are described in detail below. These examples are intended to be illustrative, and the materials, conditions, and process parameters set forth in these exemplary embodiments are not limiting. All parts and percentages are by weight unless otherwise indicated.

EXAMPLES

Comparative Example 1

Knoevenagel Reaction Using Toluene and Piperidine

Into a 2 L reaction flask equipped with nitrogen inlet, thermometer and dean stark trap, the following were charged: 152.73 g (0.4 mol) of bisformyl-N,N-diphenyl-4-aminobiphenyl, 166.5 g (1.6 mol) of malonic acid, 430 g of toluene. 136.24 g (1.6 mol) of piperidine was added drop wise to the contents. An exotherm (ΔT=40° C.) was observed upon addition of the piperidine. Once piperidine addition was complete, the reaction mixture was heated under nitrogen and stirring. Azeotropic distillation of the water byproduct began at about 97° C. and increased gradually to 114° C. The temperature was maintained for 3 hours with samples drawn intermittently. During this time toluene and piperidine were also being removed. The reaction system was then cooled to room temperature and 500 g of 10% sulfuric acid in water was gradually added. A viscous orange precipitate formed. The solid was slurried with 750 mL of isopropyl alcohol (IPA) at 50° C. for 2 hours. This helped to break up the solid into particles. The mixture was filtered and reslurried with 250 mL IPA for overnight. The solid yellow product was dried at 50° C. under vacuum. The product was analyzed by NMR. The results are set forth in the Table below.

Comparative Example 2

Knoevenagel Reaction Using Toluene and Piperazine

Into a 500 mL reaction flask equipped with nitrogen inlet, thermometer and dean stark trap, the following were charged: 15.1 g (0.04 mol) of bisformyl-N,N-diphenyl-4-aminobiphenyl, 16.65 g (0.16 mol) of malonic acid, 13.63 g (0.16 mol) of piperazine and 100 g of toluene. The reaction mixture was heated under nitrogen and stirring to achieve azeotropic distillation of the water byproduct. As the reaction progressed, sticky solids precipitated out. The temperature was maintained overnight with samples drawn intermittently. The reaction system was then cooled to room temperature and filtered. A sticky orange solid was isolated and washed with 10% sulfuric acid in water. The solid washed with PTA and dried at 50° C. under vacuum. The product was analyzed by NMR. The results are set forth in the Table below.

Comparative Example 3

Knoevenagel Reaction Using DMF and Piperidine

A process similar to Comparative Examples 1 and 2 is followed, but using the improved solvent DMF and the conventional catalyst piperidine. The results are set forth in the Table below.

Example 1

Knoevenagel Reaction Using DMF and Piperazine

Into a 1 L jacketed reactor equipped with nitrogen inlet, thermometer and dean stark trap, the following were charged: 30.2 g (0.08 mol) of bisformyl-N,N-diphenyl-4-aminobiphenyl, 20.8 g (0.2 mol) of malonic acid, 6.9 g (0.08 mol) of piperazine and 200 g of DMF. The reaction mixture was heated to 126° C. under nitrogen and stirring. The temperature was maintained for 5 hours with samples drawn intermittently. The reaction system was then cooled to 75° C. and 350 g of 10% sulfuric acid in water was gradually added. A viscous orange precipitate formed and gradually became powdery. The solids were isolated then slurried twice with 250 mL of 25% IPA in water. The solid yellow product was dried at 50° C. under vacuum. The product was analyzed by NMR. The results are set forth in the Table below.

Examples 2 and 3

Processes similar to Example 1 are followed, but using a mixture of the improved solvent DMF and conventional toluene as solvent and ammonium acetate catalyst (Example 2), or the improved solvent DMF as solvent and β-alanine catalyst (Example 3). The results are set forth in the Table below.

| Comparison of amine catalysts with and without DMF | | | | | |
|---|---|---|---|---|---|
| Example | Solvent | Catalyst | Time (h) | Yield | Aldehyde in product (NMR) |
| Comp 1 | Toluene | Piperidine | 3 | 81% | 0 |
| Comp 2 | Toluene | Piperazine | overnight | 47% | 0 |
| Comp 3 | DMF | Piperidine | 3 | 86% | 0 |
| 1 | DMF | Piperazine | 5 | 92% | 0 |
| 2 | DMF + Toluene | Ammonium Acetate | 4 | 65% | Trace |
| 3 | DMF | β-alanine | 4 | 88% | Trace |

The results indicate that for the Examples, which utilize an improved solvent and a solid catalyst system, comparable reaction time and comparable or improved yield are obtained, as compared to the Comparative Examples that use conventional solvent anchor conventional liquid catalyst systems. However, the processes of the Examples provide various of the advantages described above, including the absence of a reaction exotherm upon catalyst addition, the provision of a homogeneous mixture, possible elimination of an unnecessary azeotropic distillation, easier scale-up, and the use of safer materials.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A process for converting a first arylamine compound into a second arylamine compound, comprising:
   (i) providing a first arylamine compound;
   (ii) formylating said first arylamine compound to form a formyl substituted arylamine compound, where the first arylamine compound is not a formyl substituted arylamine compound; and
   (iii) acidifying said formyl substituted arylamine compound, in the presence of N,N-dimethylformamide as a solvent and piperazine as a catalyst, to convert formyl functional groups into acid functional groups to form an acidified compound;
   wherein; there is provided a second arylamine compound that is different from the first arylamine compound, and said first arylamine compound is a triarylamine.

2. The process according to claim 1, wherein said first arylamine compound is represented by the following general formula:

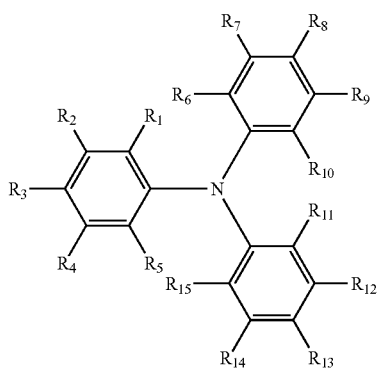

where $R^1$-$R^{15}$, which can be the same or different, are independently selected from the group consisting of hydrogen, a halogen, an alkyl group, an aryl group optionally substituted by one or more alkyl groups, an alkyl group substituted by a heteroatom, and an aryl group substituted by a heteroatom and optionally substituted by one or more alkyl groups.

3. The process according to claim 1, wherein said first arylamine compound is a disubstituted aminophenyl compound represented by the following general formula:

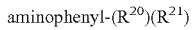

where $R^{20}$ and $R^{21}$, which can be the same or different, represent aryl groups.

4. The process according to claim 1, wherein said first arylamine compound is a disubstituted 4-aminobiphenyl compound represented by the following general formula:

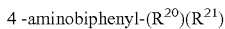

where $R^{20}$ and $R^{21}$, which can be the same or different, represent aryl groups.

5. The process according to claim 4, wherein $R^{20}$ and $R^{21}$ are aryl groups selected from the group consisting of substituted or unsubstituted phenyl groups, substituted or unsubstituted groups including two or more phenyl groups, and mixtures thereof.

6. The process according to claim 1, wherein said formylating is conducted by one of (i) a Vilsmeier reaction, (ii) treating a halogenated derivative of the first arylamine compound with n-butyllithium followed by dimethylformamide, and (iii) treating a halogenated derivative of the first arylamine compound with hexamethylene tetraamine in the presence of trifluoroacetic acid.

7. The process according to claim 1, wherein said first arylamine compound or said formyl substituted arylamine compound is a formyl substituted compound represented by the following general formula:

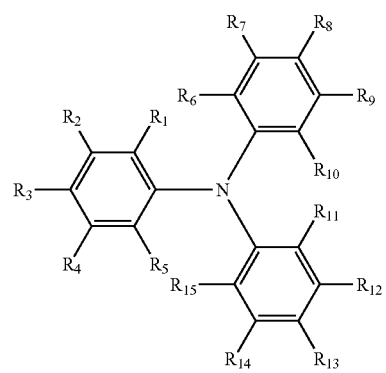

wherein $R^1$-$R^{15}$, which can be the same or different, are independently selected from the group consisting of hydrogen, a halogen, an alkyl group, an aryl group optionally substituted by one or more alkyl groups, an alkyl group substituted by a heteroatom, and an aryl group substituted by a heteroatom and optionally substituted by one or more alkyl groups, and
wherein at least or more one of the $R^1$-$R^{15}$ groups is formylated to include a terminal —CH=O group.

8. The process according to claim 7, wherein at least one group on at least two different phenyl rings is formylated to include a terminal —CH=O group.

9. The process according to claim 7, wherein at least one group on at least three different phenyl rings is formylated to include a terminal —CH=O group.

10. The process according to claim 1, wherein said first arylamine compound or said formyl substituted arylamine compound is a bisformyl substituted compound represented by the following general formula:

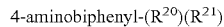

where $R^{20}$ and $R^{21}$, which can be the same or different, represent formyl -substituted aryl groups.

11. The process according to claim 1, wherein said acidifying is conducted by way of a Knoevenagel condensation reaction.

12. The process according to claim 1, wherein said acidifying converts —CH=O formyl functional end groups into —C=C—COOH carboxylic acid functional end groups.

13. The process according to claim 1, wherein said solvent solubilizes the catalyst.

14. The process according to claim 1, wherein said solvent solubilizes the reaction components catalyst, and reaction products.

15. The process according to claim 1, wherein said solvent does not also function as a catalyst in said formylating step or said acidifying step.

16. The process according to claim 1, wherein said acidifying said formyl substituted arylamine compound is further conducted in the presence of an active methylene compound.

17. The process according to claim 16, wherein said active methylene compound is selected from the group consisting of malonic acids, malonic esters, malonamides, malononitrile, cyanoacetic acid, cyanoacetic esters, cyanoacetamides, and mixtures thereof.

18. The process according to claim 1, further comprising:
(iv) hydrogenating said acidified compound to saturate at least one unsaturated double bond in the acidified compound.

19. The process according to claim 1, wherein the acidifying is conducted at a temperature above the toluene-water reflux temperature.

20. The process according to claim 1, wherein the acidifying is conducted at a temperature of from about 100° C. to about 300° C.

21. The process according to claim 1, wherein the acidifying step exhibits no exotherm or an exotherm of less than about 10° C.

22. The process according to claim 1, wherein water is not removed from the reaction by azeotropic distillation during the acidifying step.

23. A process for converting a first 4-aminobiphenyl arylamine compound into a second 4-aminobiphenyl arylamine compound, comprising:
(i) providing a first disubstituted 4-aminobiphenyl compound;
(ii) formylating said first disubstituted 4-aminobiphenyl compound to form a bisformyl substituted compound, where said first disubstituted 4-aminobiphenyl compound is not a bisformyl substituted compound; and
(iii) acidifying said bisformyl substituted compound, in the presence of dimethylformamide as a solvent and piperazine as a catalyst, to convert formyl functional groups into acid functional groups to form an acidified compound;
wherein; there is provided a second disubstituted 4-aminobiphenyl compound that is different than the first disubstituted 4-aminobiphenyl compound.

24. The process according to claim 23, wherein said second disubstituted 4-aminobiphenyl compound is a carboxylic acid compound.

25. The process according to claim 23, wherein said second disubstituted 4-aminobiphenyl compound is represented by the following general formula:

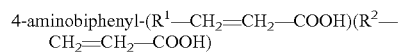

where $R^1$ and $R^2$, which can be the same or different, represent aryl groups.

26. The process according to claim 1, wherein the catalyst is added to the reaction in a solid form.

27. The process according to claim 23, wherein the catalyst is added to the reaction in a solid form.

* * * * *